(12) United States Patent
Okoniewski

(10) Patent No.: US 8,298,188 B2
(45) Date of Patent: Oct. 30, 2012

(54) TELESCOPING CANNULA

(75) Inventor: Gregory G. Okoniewski, North Haven, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 87 days.

(21) Appl. No.: 12/898,053

(22) Filed: Oct. 5, 2010

(65) Prior Publication Data

US 2011/0021880 A1 Jan. 27, 2011

Related U.S. Application Data

(63) Continuation of application No. 12/400,912, filed on Mar. 10, 2009, now Pat. No. 7,828,775.

(60) Provisional application No. 61/044,183, filed on Apr. 11, 2008.

(51) Int. Cl.
*A61M 5/178* (2006.01)
(52) U.S. Cl. .................................. 604/167.01
(58) Field of Classification Search .............. 604/23–26, 604/506, 93.01, 158, 164.01, 164.02, 164.11, 604/165.02–165.04, 166.01, 167.01, 264, 604/272, 110, 111, 192
See application file for complete search history.

(56) References Cited

U.S. PATENT DOCUMENTS

| | | | |
|---|---|---|---|
| 5,383,860 A | 1/1995 | Lau | |
| 5,569,290 A | 10/1996 | McAfee | |
| 5,674,240 A | 10/1997 | Bonutti et al. | |
| 5,814,073 A | 9/1998 | Bonutti | |
| 5,882,344 A * | 3/1999 | Stouder, Jr. | 604/264 |
| 5,944,691 A | 8/1999 | Querns et al. | |
| 5,957,888 A | 9/1999 | Hinchliffe | |
| 6,197,002 B1 | 3/2001 | Peterson | |
| 2004/0087968 A1 | 5/2004 | Core | |
| 2004/0260246 A1 | 12/2004 | Desmound | |
| 2005/0096507 A1 | 5/2005 | Prosek | |
| 2006/0033333 A1* | 2/2006 | Pickney | 285/386 |
| 2006/0200185 A1 | 9/2006 | Marchek et al. | |

FOREIGN PATENT DOCUMENTS

| | | |
|---|---|---|
| EP | 1 454 590 A1 | 9/2004 |
| WO | WO 00/45720 | 8/2000 |
| WO | 03/011154 A2 | 2/2003 |

OTHER PUBLICATIONS

Extended International Search Report corresponding to European Application No. EP 09 25 1068.4, completed Jun. 17, 2009; mailed Jun. 25, 2009; 3 pages.
Extended International Search Report corresponding to European Application No. EP 10 25 0720.9, completed Jul. 19, 2010; mailed Jul. 27, 2010; 3 pages.

* cited by examiner

*Primary Examiner* — Christopher D Koharski

(57) ABSTRACT

An apparatus may serve as a surgical portal for the reception of surgical instruments for use in laparoscopic or similar surgery. The apparatus may include inner and outer tubular elongate members adapted for a longitudinal translation relative to one another to effect a length adjustment of the apparatus. An interface between the two elongate members includes a helical thread providing a mechanism for the translation of the elongate members, and indentations in one of the members provides a locking mechanism for affixing the length.

6 Claims, 2 Drawing Sheets

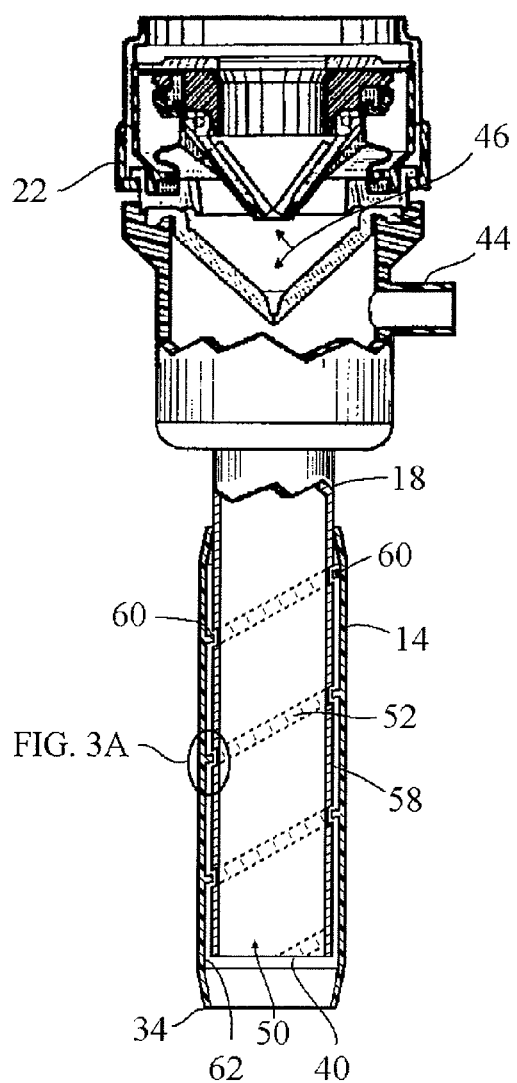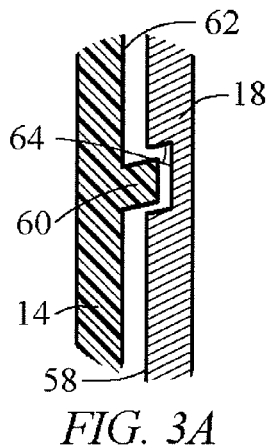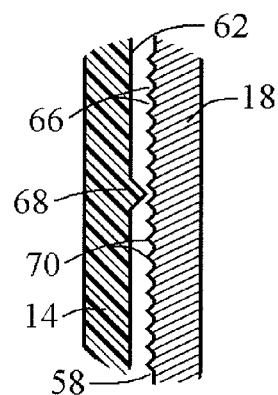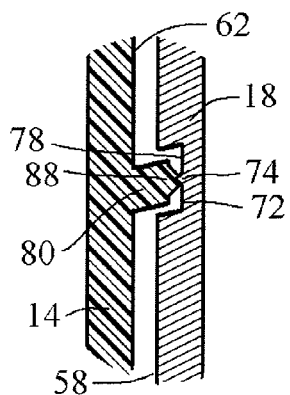
FIG. 2
FIG. 3A
FIG. 3B
FIG. 3C

TELESCOPING CANNULA

CROSS REFERENCE TO RELATED APPLICATIONS

The present application is a Continuation of U.S. patent application Ser. No. 12/400,912, filed Mar. 10, 2009 now U.S. Pat. No. 7,828,775, which claims priority to U.S. Provisional Patent Application Ser. No. 61/044,183, filed on Apr. 11, 2008, the entire content of each of these applications being incorporated herein by reference.

BACKGROUND

1. Technical Field

The present disclosure relates generally to an apparatus for permitting the introduction of a surgical instrument into a patient's body cavity in a laparoscopic or similar surgery. In particular, the disclosure relates to a telescoping cannula assembly configured for longitudinal extension and retraction to effect a length adjustment.

2. Background of Related Art

A relatively small incision is required for minimally invasive surgical procedures such as laparoscopic, arthroscopic, and endoscopic procedures as compared with conventional open procedures. Small incisions are preferred because they are inherently less traumatic to the body tissue and subject internal organs to a minimum of exposure to contaminants in the outside atmosphere. Thus, small incisions enable shorter hospital stays and faster recoveries with less pain and scarring than is common with the larger incisions required for conventional surgery.

Minimally invasive surgery is possible due in part to the availability of instruments designed specifically for this purpose. A cannula, for example, is an elongated tube that may be inserted through the small incision made in a body cavity wall of a patient to provide a working conduit between an internal body cavity adjacent an operative site and the environment exterior to the patient. The body cavity is often inflated with an insufflation gas such as carbon dioxide to separate the body cavity wall from vital organs and to provide some space where a distal end of the cannula can safely protrude into the patient below the body cavity wall.

The length of a cannula is generally selected to span a range of anatomies and consequently a portion of the cannula assembly which remains on the outside of the patient may extend above the body cavity wall to a greater extent than otherwise desired. The cannula assembly may need to extend into deeper regions of the body cavity, e.g., the abdominal cavity, to access remote underlying organs therein. Furthermore, because several instruments of various lengths might be required for a surgical procedure, an instrument may protrude above the cannula assembly to a greater extent than otherwise desired. Accordingly, a need exists for a cannula assembly which facilitates the introduction of surgical instruments to a surgical site, while allowing a longitudinal retraction or extension to effect an adjustment in length.

SUMMARY

The present disclosure describes a surgical portal apparatus which permits a length adjustment to accommodate a range of body cavity wall thicknesses. The apparatus comprises a tubular elongate inner member adapted and sized appropriately for the introduction of a surgical instrument. The elongate inner member has a proximal end, a distal end and a length therebetween, with a portion of the length radially surrounded by a tubular elongate outer member. A length adjustment structure provides an adjustment interface between the elongate inner member and the elongate outer member. The length adjustment structure includes a generally helical thread on at least one of the elongate members and feature on the other for engaging the thread. A length fixation structure includes inter-engaging components for selectively and non-permanently securing a longitudinal position of the elongate inner member within the elongate outer member.

The inter-engaging components may include a series of indentations arranged in a generally helical pattern corresponding to the generally helical thread. The series of indentations may be disposed on an interior surface of the generally helical thread. The surgical portal apparatus may include a housing at or near the proximal end containing a seal apparatus capable of sealing the apparatus before, during and after the introduction of a surgical instrument. The housing may include a connection for introducing an insufflation gas into the body cavity. The elongate outer member may be positioned distally of the elongate inner member.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 2 is a partial cross-sectional view of the telescoping cannula assembly of FIG. 1;

FIG. 3A is an enlarged view of the area of detail identified in FIG. 2;

FIG. 3B is a view similar to view 3A depicting an alternate length fixation structure; and FIG. 3C is a view similar to view 3A depicting another alternate length fixation structure.

DETAILED DESCRIPTION OF PREFERRED EMBODIMENTS

Figure 1:
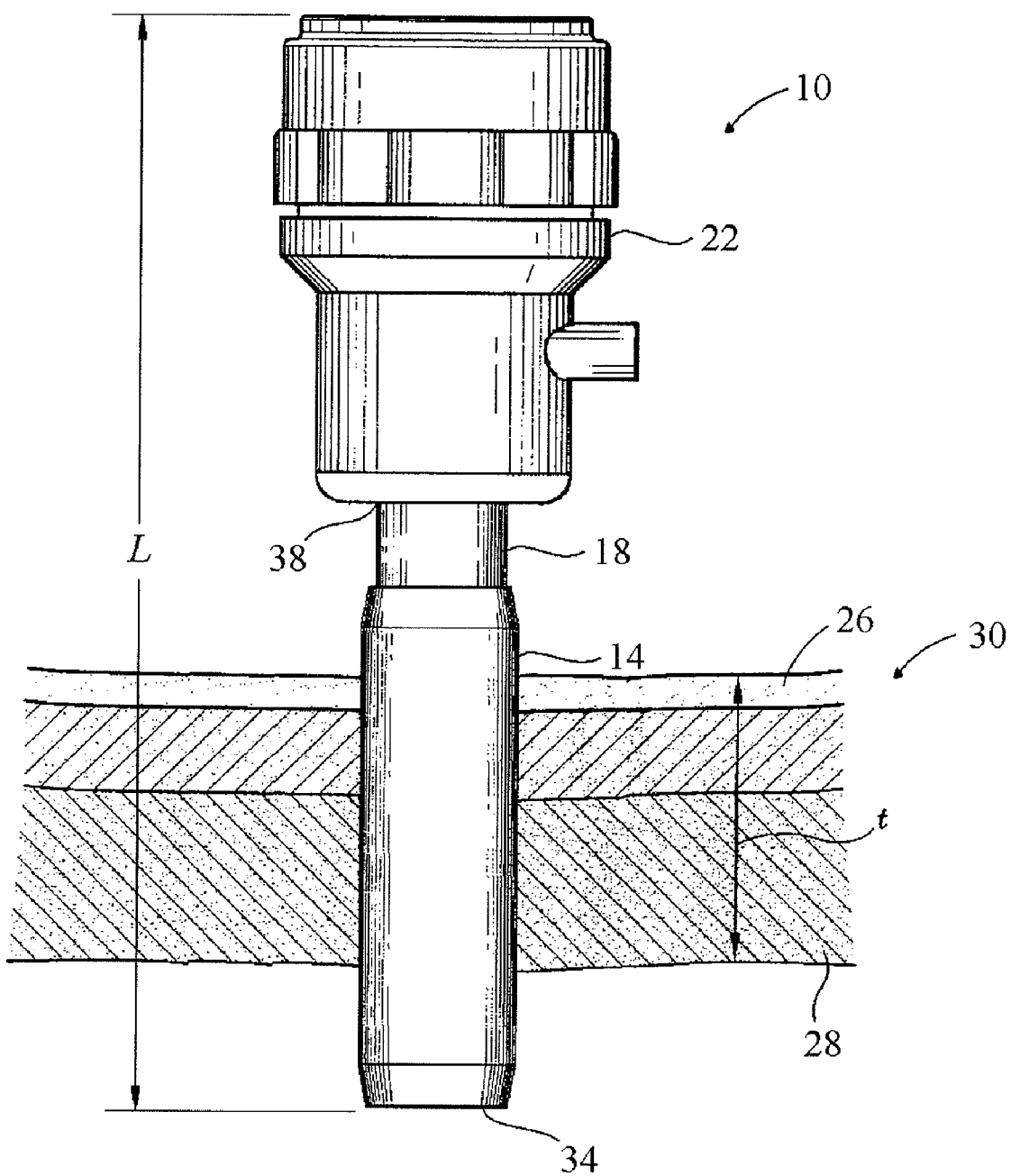
FIG. 1 is a side view of a surgical portal apparatus in accordance with the present disclosure inserted through a body cavity wall.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein generally as "instruments." In the drawings and in the description that follows, the term "proximal," as is traditional, will refer to the direction toward the operator or a relative position on the surgical device or instrument that is closer to the operator, while the term "distal" will refer to the direction away from the operator or relative position of the instrument that is further from the operator.

Referring initially to FIG. 1, a surgical portal apparatus is generally depicted as telescoping cannula assembly 10. Telescoping cannula assembly 10 includes an elongate outer member 14, an elongate inner member 18 and a housing 22. Elongate outer member 14 is positioned through the skin 26 and within a layer of body tissue 28. Skin 26 and body tissue 28 together define a body cavity wall 30 with a thickness "t." A distal end 34 of the elongate outer member 14 protrudes into an interior body cavity of a patient, and housing 22 remains in an exterior environment. A proximal end 38 of elongate inner member 18 may be rigidly coupled to housing 22 such that there is no relative motion therebetween, and a distal end 40 (FIG. 2) of inner member 18 is telescopically arranged within elongate outer member 14. Using a length adjustment structure as described in greater detail below, the overall length "L" of telescoping cannula assembly 10 may be adjusted by retracting or extending elongate inner member 18, for example to accommodate a variance in the thickness "t" of body cavity wall 30.

Referring now to FIG. 2, telescoping cannula assembly 10 is depicted in partial cross section. Housing 22 includes an insufflation gas valve 44 and internal seal system 46, which may be capable of permitting the passage of an instrument while preventing insufflation gasses from escaping through a proximal end of telescoping cannula assembly 10 before, during and after introduction of the instrument. Internal seal system 46 may take any form including the form described in U.S. Pat. No. 5,603,702 to Smith et al., filed Aug. 8, 1994, the entire contents of which are hereby incorporated by reference.

Elongate inner member 18 includes a longitudinal bore 50 defining a passageway adapted for the introduction of an instrument. The distal end 40 and a substantial portion of elongate inner member 18 are radially surrounded by elongate outer member 14. A length adjustment structure defines the degree to which elongate inner member 18 is nested within elongate outer member 14 and therefore, the overall length L of telescoping cannula assembly 10.

The length adjustment structure may include a female thread 52 (shown in phantom) disposed on an outer surface 58 of elongate inner member 18. A corresponding male protrusion 60 or rib is disposed on an interior surface 62 of elongate outer member 14 and extends into thread 52. Male protrusion 60 may take the form of a full male thread. Alternatively, male protrusion 60 may comprise one or more narrow tabs appropriately positioned to guide the relative motion of elongate outer member 14 along thread 52. As seen best in FIG. 3A, thread 52 includes several interior surfaces 64 for engaging male protrusion 60. Thread 52 may exhibit a course pitch allowing for large adjustments to be made quickly requiring only a few rotations of either the inner or outer elongate member 18, 14. The overall length of cannula assembly may be adjusted by corresponding rotational movement of inner member 18 and outer member 14.

As seen in FIG. 3B, a length fixation structure may comprise a series of indentations 66 on the exterior surface 58 of elongate inner member 18. Indentations 66 may be discrete, incrementally spaced notches or serrations arranged along the length of elongate inner member 18. Male rib 68 may extend into an indentation 66 to non-permanently arrest the relative motion of elongate inner and outer members 14, 18. When sufficient force is applied to either the elongate inner or outer member 14, 18 in an axial direction, male rib 68 may be temporarily displaced to move over ridges 70 between indentations 66. In this way, male rib 68 can act as a pawl engaging a ratchet formed from the series of indentations 66 and ridges 70 to non-permanently fix the overall length "L" of cannula assembly 10. Male rib 68 may be formed from a flexible material, ball plunger, or other suitable arrangement. Indentations 66 and male rib 68 may encircle elongate inner member or any part thereof.

Referring now to FIG. 3C, a length adjustment interface is described that incorporates a length adjustment structure and a length fixation structure. A helical thread 72 wraps around elongate inner member 18. Helical thread 72 is equipped with a series of internal spaced ridges or detents 74 and indentations (not visible) between ridges 74 arranged along a helical path corresponding to an inner surface 78 of thread 72. Male protrusion 80 is equipped with male rib or pawl 88 configured to interface with the indentations between ridges 74 in, e.g., a pawl detent arrangement or in the manner described in connection with the embodiment of FIG. 3B. Male protrusion 80 may alternatively be adapted to engage the indentations between ridges 74 directly.

The positioning of the indentations may take various forms. For example, the indentations may be positioned in a helical path on the outside surface 58 of elongate inner member 18 rather than on an inside surface 78 of thread 72. In this case a male rib 88 on the inside surface 62 of elongate outer member may engage the indentations to secure the relative positions of elongate members 14, 18. Also, rather than resembling closely spaced serrations, the indentations may comprise a limited number of strategically placed detents to accommodate the use of standard sized instruments or to accommodate the most typical tissue thicknesses.

In use, the overall length "L" of telescoping cannula 10 may be adjusted by rotating elongate inner member 18 along thread 72 until elongate inner member 18 reaches a satisfactory longitudinal position within elongate outer member 14. The engagement of male rib 88 with an indentation may provide a tactile queue that such a position has been achieved. The engagement of male rib 88 is sufficiently robust to prevent any unintended longitudinal migration of elongate inner member 18 under the weight of housing 22 and other forces associated with introducing and manipulating a surgical instrument.

In drawing figures and the corresponding descriptions above, the male features of the adjustment interface have been associated with the elongate outer member 14 and the female components have been associated with the elongate inner member 18. However, this convention made for clarity may be reversed and these features may be associated with either elongate member 18, 14. Also, the elongate inner member has been described as fixedly attached to the housing 22 and the elongate outer member movable relative to the housing and elongate inner member. This convention may also be reversed such that the elongate outer member is fixedly attached to the housing and the elongate inner member is movable within the elongate outer member 14.

Although the foregoing disclosure has been described in some detail by way of illustration and example, for purposes of clarity or understanding, it will be obvious that certain changes and modifications may be practiced within the scope of the appended claims.

What is claimed is:

1. A method of surgically accessing a body cavity through a body cavity wall, the method comprising the steps of:
providing an adjustable surgical portal apparatus including an inner member nested within an outer member, wherein the inner and outer members engage one another by a helical thread defined on at least one of the inner and outer members, and wherein a plurality of incrementally spaced indentations are defined along the helical between a proximal end and a distal end of the helical thread for releasably engaging a locking element defined on the other of the inner and outer members;
rotating the inner and outer members with respect to one another to displace the locking element from a first of the plurality of incrementally spaced indentations and subsequently engage the locking element with a second of the indentations to adjust the relative longitudinal positioning of the inner and outer members such that the overall length of the portal apparatus is appropriate to accommodate the thickness of the body cavity wall; and inserting a distal end of the surgical portal apparatus through the body cavity wall into the body cavity.

2. The method according to claim 1, wherein the step or rotating the inner and outer members displaces the locking element from a plurality of the incrementally spaced indentations before subsequently engaging with the second of the indentations.

3. The method according to claim 1, wherein the step of rotating the inner and outer members includes rotating the inner and outer members about a longitudinal axis defined by inner member.

4. The method according to claim 1, further comprising the step of introducing an instrument through a passageway defined through the inner and outer members of the surgical portal apparatus.

5. The method according to claim 4, wherein the step of introducing an instrument includes forming a seal between the instrument and an internal seal system provided with the surgical portal apparatus.

6. A method of surgically accessing a body cavity through a body cavity wall having a thickness, the method comprising the steps of:

providing an adjustable surgical portal apparatus including an inner member nested within an outer member, wherein the inner and outer members engage one another by a helical thread defined on at least one of the inner and outer members, and wherein a plurality of incrementally spaced indentations are defined along the helical thread between a proximal end and a distal end of the helical thread for releasably engaging a locking element defined on the other of the inner and outer members;

determining an appropriate overall length of the portal apparatus to accommodate the thickness of the body cavity wall rotating the inner and outer members with respect to one another to displace the locking element from a first of the plurality of incrementally spaced indentions;

continuing to rotate the inner and outer members to engage and displace the locking element with an appropriate number of the indentations to adjust the overall length of the portal apparatus to the appropriate overall length of the portal apparatus; and inserting a distal end of the surgical portal apparatus through the body cavity wall into the body cavity.

* * * * *